(12) United States Patent
Huang et al.

(10) Patent No.: US 12,392,745 B2
(45) Date of Patent: Aug. 19, 2025

(54) CAPACITIVE SOIL MOISTURE DETECTION DEVICE AND SYSTEM

(71) Applicant: Fujian Tiancheng Baode Intelligent Technology Co., Ltd., Fuzhou (CN)

(72) Inventors: Zhongdong Huang, Fuzhou (CN); Jie Yang, Fuzhou (CN)

(73) Assignee: Fujian Tiancheng Baode Intelligent Technology Co., Ltd., Fuzhou (CN)

( * ) Notice: Subject to any disclaimer, the term of this patent is extended or adjusted under 35 U.S.C. 154(b) by 157 days.

(21) Appl. No.: 18/532,179

(22) Filed: Dec. 7, 2023

(65) Prior Publication Data

US 2025/0137961 A1    May 1, 2025

(30) Foreign Application Priority Data

Oct. 27, 2023 (CN) .......................... 202311409919.1

(51) Int. Cl.
 *G01N 27/22* (2006.01)
 *G01N 33/24* (2006.01)

(52) U.S. Cl.
 CPC ......... *G01N 27/223* (2013.01); *G01N 27/226* (2013.01); *G01N 27/227* (2013.01); *G01N 33/24* (2013.01)

(58) Field of Classification Search
 CPC .. G01N 27/223; G01N 27/226; G01N 27/227; G01N 33/24; G01N 33/246; G01N 27/22
 See application file for complete search history.

(56) References Cited

U.S. PATENT DOCUMENTS

| | | | | |
|---|---|---|---|---|
| 2006/0096370 A1* | 5/2006 | Isogai | ................ | G01N 27/223 73/335.04 |
| 2015/0047430 A1* | 2/2015 | Benzel | ................ | G01N 27/225 438/49 |
| 2015/0330932 A1* | 11/2015 | Kumaran | ............ | G01N 27/223 324/664 |
| 2018/0284048 A1* | 10/2018 | Wakana | ................ | G01N 27/22 |
| 2024/0402117 A1* | 12/2024 | Beck | ................... | G01N 27/223 |

FOREIGN PATENT DOCUMENTS

CN         207516300 U      6/2018

* cited by examiner

*Primary Examiner* — Alvaro E Fortich
(74) *Attorney, Agent, or Firm* — Birchwood IP

(57) ABSTRACT

The present disclosure discloses a soil moisture detection device and system. By providing with an outer shell and providing with a circuit board and a main control chip in the outer shell, an end of a substrate is clamp connection to the outer shell, an inner of the substrate is provided with at least two electrode pieces. Two electrode pieces are facing to each other and have a gap between herein. At the same time, each electrode piece is coated with a substrate material to form a capacitive structure, which can have a larger capacitance, according to a humidity change of the soil, it can generate a corresponding capacitance change more sensitively, thereby improving a measurement accuracy and benefiting to achieve a more precise control of environmental soil moisture.

20 Claims, 5 Drawing Sheets

CAPACITIVE SOIL MOISTURE DETECTION DEVICE AND SYSTEM

CROSS-REFERENCE TO RELATED APPLICATIONS

This application claims priority to Chinese Patent Application No. 202311409919.1, filed on Oct. 27, 2023, which is hereby incorporated by reference in its entirety.

TECHNICAL FIELD

The present disclosure relates to the field of soil moisture detection technologies, and in particular, to a capacitive soil moisture detection device and system.

BACKGROUND

The common types of soil hygrometers include resistance type, capacitance type, and ion type. The capacitance type soil hygrometers convent capacitance changes as a change of a capacitor in a substrate caused by humidity changes of the soil into a corresponding electrical signal to achieve the moisture detection of the soil.

The common structure of the substrate of existing capacitive soil hygrometers is provided with a U-shaped electrode and a I-shaped electrode in the substrate, and the U-shaped electrode is wrapped around an outer side of the I-shaped electrode, and a capacitance is formed between the two. The capacitance between the two is changed by the humidity change of the soil. For example, CN207516300U, entitled with "capacitive soil moisture sensor", which includes a housing in thin-shell shape, a power conversion module, a moisture measurement circuit, a capacitive probe and a data interface, a lower end of the housing is a V-shaped tip, the data interface is located on the housing, the capacitive probe is located in a middle of the housing, the capacitive probe is connected to the moisture measurement circuit, and the power conversion module is connected to the moisture measurement circuit and the data interface. Compared to the resistance type soil hygrometers, this type has the advantages of being less prone to corrosion and having stable and reliable performance. However, due to a limited structure size of the capacitor, a detection accuracy of soil moisture may be affected, and it may not be able to detect small changes in soil moisture.

SUMMARY

Therefore, it is necessary to provide a capacitive soil moisture detection device and system to solve the problem that a capacitance structure of existing soil hygrometers which limit the size of the capacitance, and in turn affects a detection accuracy of soil moisture and may not be able to detect small changes in soil moisture.

To achieve the above objectives, the present disclosure provides a capacitive soil moisture detection device, which includes a substrate, an outer shell, a circuit board, and a main control chip;

the main control chip is provided on the circuit board, the circuit board is provided with a moisture measurement circuit that is arranged in the outer shell; a connection end of the substrate is clamp connection to the outer shell;

an inner of the substrate is provided with at least two electrode pieces, the electrode pieces are facing to each other and arranged spaced apart; each electrode piece is coated with a substrate material; a pin of one of the electrode pieces is connected to the main control chip, and an adjacent other electrode piece is provided with a grounding terminal.

In an implementation mode of the present disclosure, the substrate is a PCB board.

In an implementation mode of the present disclosure, the substrate includes a front plate, a middle plate, and a rear plate.

In an implementation mode of the present disclosure, the substrate is provided with a series of holes, which are arranged along an edge of the substrate, or an outer surface of the substrate is covered with a reinforcing layer.

In an implementation mode of the present disclosure, the moisture measurement circuit further includes a first resistor, a pin of one of the electrode pieces is respectively connected to a detection pin of the main control chip and an end of the first resistor; the other end of the first resistor is connected to a signal output pin of the main control chip.

In an implementation mode of the present disclosure, the moisture measurement circuit further includes:
 a first capacitor, a pin of one of the electrode pieces is respectively connected to a detection pin of the main control chip and an end of the first resistor through the first capacitor; or
 a second capacitor, two ends of the second capacitor are respectively connected to a pin of one of the electrode pieces and the grounding terminal of another one of the electrode pieces; or
 a second resistor, an end of the second resistor is connected to an end of the first resistor, and the other end of the second resistor is connected to another signal output pin of the main control chip.

In an implementation mode of the present disclosure, the moisture measurement circuit further includes a frequency square wave chip and a third resistor, a first capacitor pin of the frequency square wave chip is connected to one of the electrode pieces, an adjacent other electrode piece is connected to an end of the third resistor, and the other end of the third resistor is connected to a second capacitor pin of the frequency square wave chip; a frequency output pin of the frequency square wave chip is connected to a frequency reception pin of the main control chip.

In an implementation mode of the present disclosure, the moisture measurement circuit further includes a selection chip, a first regulating capacitor group, and a second regulating capacitor group; an access pin of the selection chip is connected to the first capacitor pin of the frequency square wave chip;
 an end of the first regulating capacitor group is connected to a first output pin of the selection chip and one of the electrode pieces, and the other end of the first regulating capacitor group is connected to a second capacitor pin of the frequency square wave chip and the other adjacent electrode piece;
 an end of the second regulating capacitor group is connected to the first output pin of the selection chip and one of the electrode pieces, the other end of the second regulating capacitor group is connected to the second capacitor pin of the frequency square wave chip and the other adjacent electrode piece.

In an implementation mode of the present disclosure, the frequency square wave chip includes multiple different division pins, and the detection pin of the main control chip is connected to one of the division pins.

The present disclosure further provides a detection system, which includes the soil moisture detection device as described in any one of the above.

Different from existing technologies, the above technical solution involves providing with a shell and providing with a circuit board and a main control chip in the shell. An end of the substrate is connected to the shell, and at least two electrode pieces are provided in the substrate. Two electrode pieces are face-to-face and have a gap. At the same time, the electrode pieces are covered by a substrate material to form a capacitive structure, which can have a larger capacitance, according to humidity changes of the soil, it can generate corresponding capacitance changes more sensitively, thereby improving a measurement accuracy and helping to achieve a more precise control of environmental soil moisture.

Figure 1:
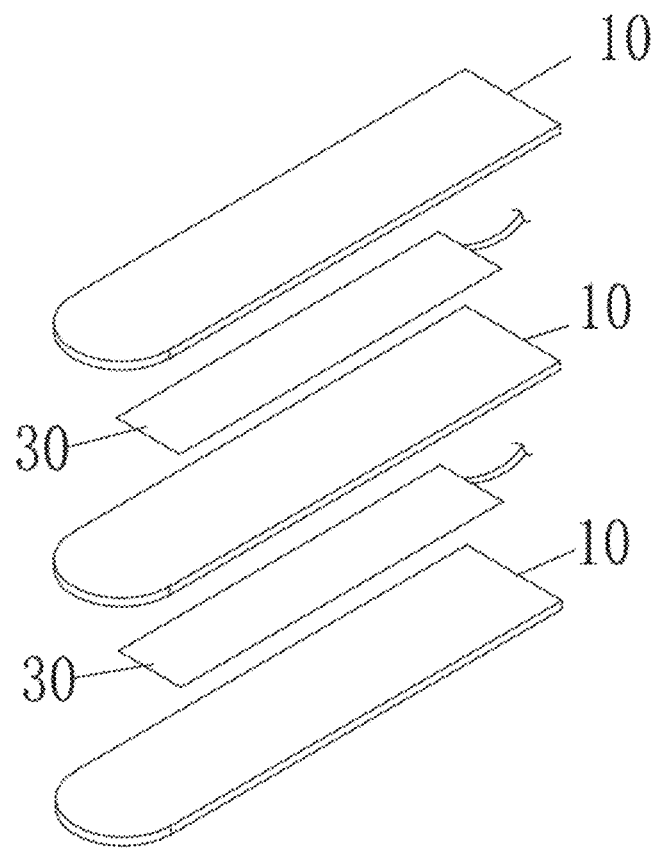
FIG. 1 is an explosive structure diagram of a substrate.
Figure 2:
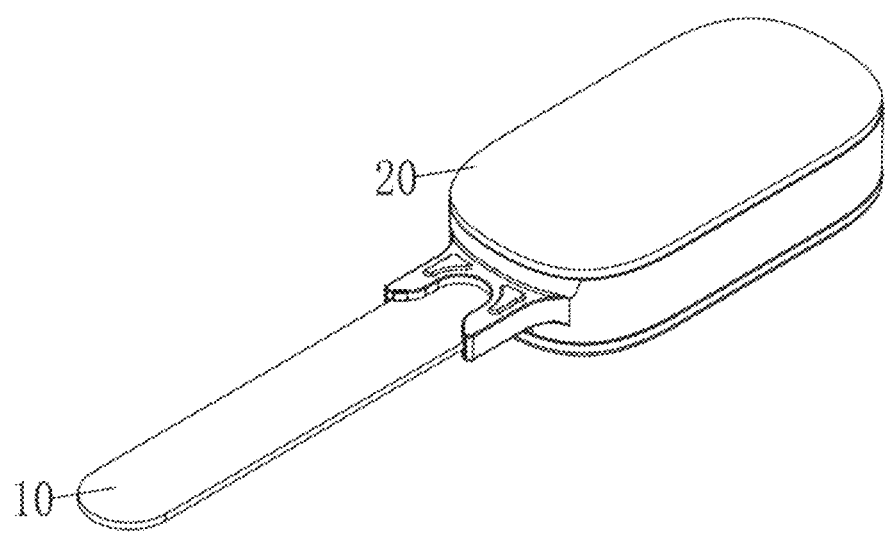
FIG. 2 is a perspective view of a detection device.

Numeral reference: 1. Substrate; 20. Shell; 30. Electrode piece.

DESCRIPTION OF EMBODIMENTS

To provide a detailed explanation of the technical solution, structural features, achieved objectives, and effects of the present disclosure, the following is a detailed explanation combined with specific embodiments and drawings.

Please refer to FIGS. 1 to 6. The present disclosure provides a capacitive soil moisture detection device, which includes a substrate 10, an outer shell 20, a circuit board, and a main control chip. In an implementation mode of the present disclosure, the substrate 10 is a PCB board, which has high reliability and stability, and is equipped with mature processing technology and process system, and thereby it is easy to process and produce, and has low cost. The main control chip is provided on the circuit board, the circuit board is provided with a moisture measurement circuit and is arranged in the shell 20. The circuit board is further provided with a circuit for corresponding button, a low point moisture measurement circuit, a LED circuit, a binding function circuit, an EEPROM (Electrically Erasable Programmable read only memory) circuit, a power circuit, and a storage circuit to achieve various corresponding functions. Specific circuit structures can refer to existing technology. A connection end of the substrate 10 is clamp connection to the shell 20, and the other end away from the connection end of the substrate 10 can be arranged in a V-shaped sharp angle or U-shaped are shape for easy insertion into the soil. The substrate 10 is internally provided with at least two electrode pieces 30. Generally speaking, providing with two electrode pieces 30 can form a capacitive structure. Specifically, it can be provided with three electrode pieces 30 or more, and a capacitive structure can also be formed. In an implementation mode of the present disclosure, the electrode piece 30 is a coper foil. Copper foil is an excellent conductive material with excellent conductivity, and after being processed by rolling technology, it has high strength and toughness, and can withstand certain stresses and loads. The electrode piece 30 are face-to-face and arranged spaced apart, and each electrode piece 30 is coated with a material of substrate 30, that is, the two electrode pieces 30 are separated by the substrate 10 material; and thus, a capacitive structure is formed. Specifically, the substrate 10 includes a front plate, a middle plate, and a rear plate, and the two electrode pieces 30 are respectively arranged on two sides of the middle plate. The front plate and the rear plate are respectively covered on two sides of the middle plate, and areas of the front plate and the rear plate are not less than an area of the electrode piece 30. For the convenience of production, a shape of the front plate and a shape of the rear plate are the same. One pin of one of the electrode pieces 30 is connected to the main control chip, and an adjacent other electrode piece 30 is provided with a grounding terminal. The working process of this embodiment is as follows: device power is turn on, the device is calibrated, the substrate 10 is inserted into the soil, a capacitance between two electrode pieces 30 is adjusted to a certain value through the main control chip, and real-time detection of the capacitance is performed. When the soil humidity changes, charge carrying capacity in the soil changes accordingly, thereby affecting the capacitance of the capacitance structure formed by a combination of electrode pieces 30 in the substrate 10, and causing a change in its capacitance, corresponding electrical signal generated by the capacitance change between the electrode pieces 30 is received by the main control chip, and conversion calculations are performed to obtain a corresponding humidity data, and thus, a moisture detection is achieved. It should be noted that in this embodiment, a physical switch button can be provided with, and a wireless module can be provided with to control the switch and receive data through a remote terminal.

The present disclosure involves providing with the shell 20 and providing with a circuit board and a main control chip in the shell 20. An end of the substrate 10 is clamp connection to the shell 20, and at least two electrode pieces 30 are provided in the substrate 10. Two electrode pieces 30 are face-to-face and have a gap between herein. At the same time, the electrode pieces 30 are covered by the substrate 10 material to form a capacitive structure, which can have a larger capacitance, according to the humidity change of the soil, it can generate corresponding a capacitance change more sensitively, thereby improving a measurement accuracy and helping to achieve a more precise control of environmental soil moisture.

Due to the fact that substrate 10 needs to be inserted into the soil for a long time and is mounted in a multi-layer structure, it may be subject to water vapor intrusion or thermal expansion and contraction, and thus, resulting in cracks. In order to make the substrate 10 more stable and tightly adhered between layers, in some embodiments, the substrate 10 is provided with a series of holes that are arranged along an edge of the substrate 10. The process of holes is a conventional PCB circuit board processing technology, which is relatively mature, and the processing cost is not high, it can effectively improve the bonding stability between the layers of the substrate 10. In other embodiments, an outer surface of the substrate 10 is covered with a reinforcing layer, which can be a protective film, such as a polytetrafluoroethylene film or a polyimide film. The protective film can achieve waterproof, dustproof, and corrosion-resistant effects; or it may be a protective agent such as epoxy resin, polyurethane, etc. can be sprayed or dipped to cover the outer surface of substrate 10, thereby achieving a comprehensive protection.

Figure 3:
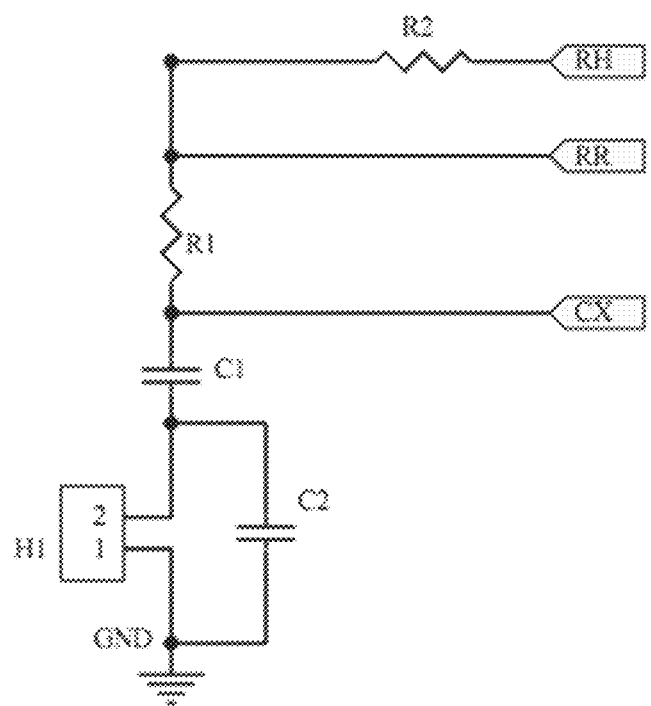
FIG. 3 is a partial structural diagram of a moisture measurement circuit according to a specific implementation mode.
Figure 4:
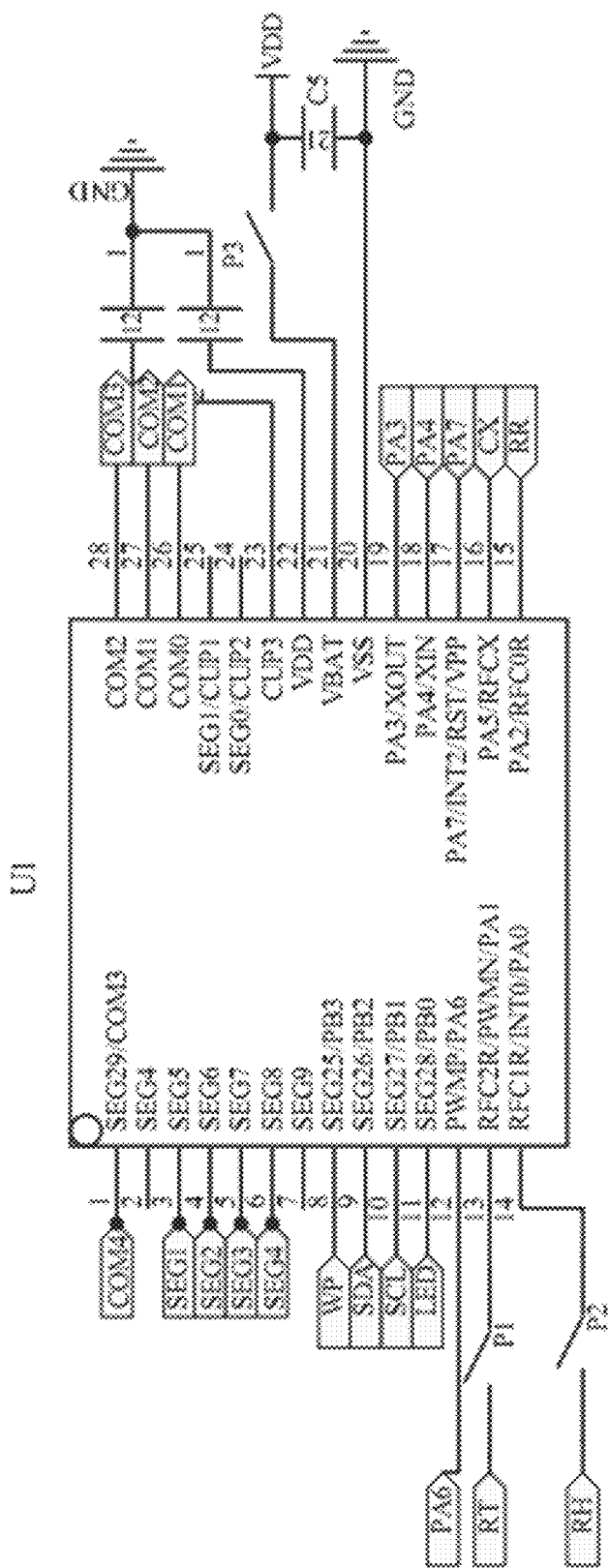
FIG. 4 is a structure diagram of a pin of a main control chip according to a specific implementation mode.
Figure 5:
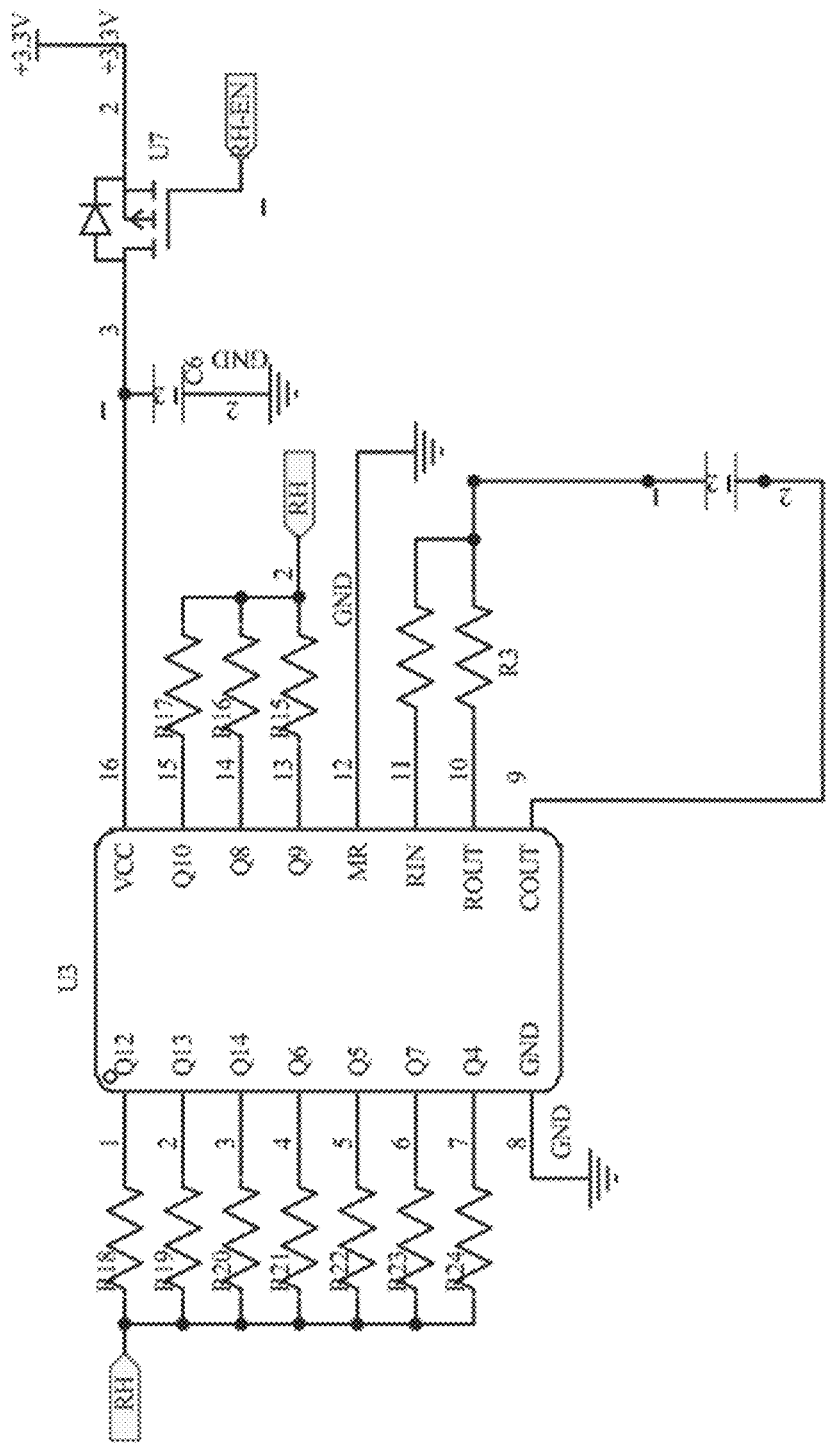
FIG. 5 is a circuit structure diagram of the moisture measurement circuit with a frequency square wave chip according to a specific implementation mode.

In some embodiments, referring to FIGS. 3-4, the moisture measurement circuit further includes a first resistor (FIG. 3, R1), a pin of one of the electrode pieces 30 is respectively connected to a detection pin (FIG. 4, U1-PA5) of the main control chip, an end of the first resistor, and the other end of the first resistor is connected to a signal output pin (FIG. 4, U1-PA2) of the main control chip. The signal output pin of the main control chip sends a square wave signal with a certain frequency to reach the electrode pieces 30 through the first resistor to charge the capacitor. When the capacitance of the capacitor is affected by soil moisture, the main control chip detects voltage changes through the detection pin and obtains corresponding humidity data by calculating the voltage changes. In an implementation mode, the moisture measurement circuit further includes a first capacitor (FIG. 3, C1), and pins of the electrode pieces 30 are connected to the detection pin of the main control chip and an end of the first resistor through the first capacitor. That is, the first capacitor is arranged in series, and a total capacitance can be adjusted through the first capacitor to achieve an effect of adjusting a size of current, avoiding instantaneous excessive current and damaging electronic components. In an implementation mode, the moisture measurement circuit further includes a second capacitor (FIG. 3, C2), two ends of the second capacitor are respectively connected to the pin of one of the electrode pieces 30 and the grounding terminal of another one of the electrode pieces 30, that is, the second capacitor is arranged in parallel and has a same function as the first capacitor. This will not be repeated here. In an implementation mode, the moisture measurement circuit further includes a second resistor (FIG. 3, R2), an end of the second resistor is connected to an end of the first resistor, and the other end of the second resistor is connected to another signal output pin of the main control chip. The current value is adjusted through the second resistor to ensure a stable operation of the circuit.

Figure 6:
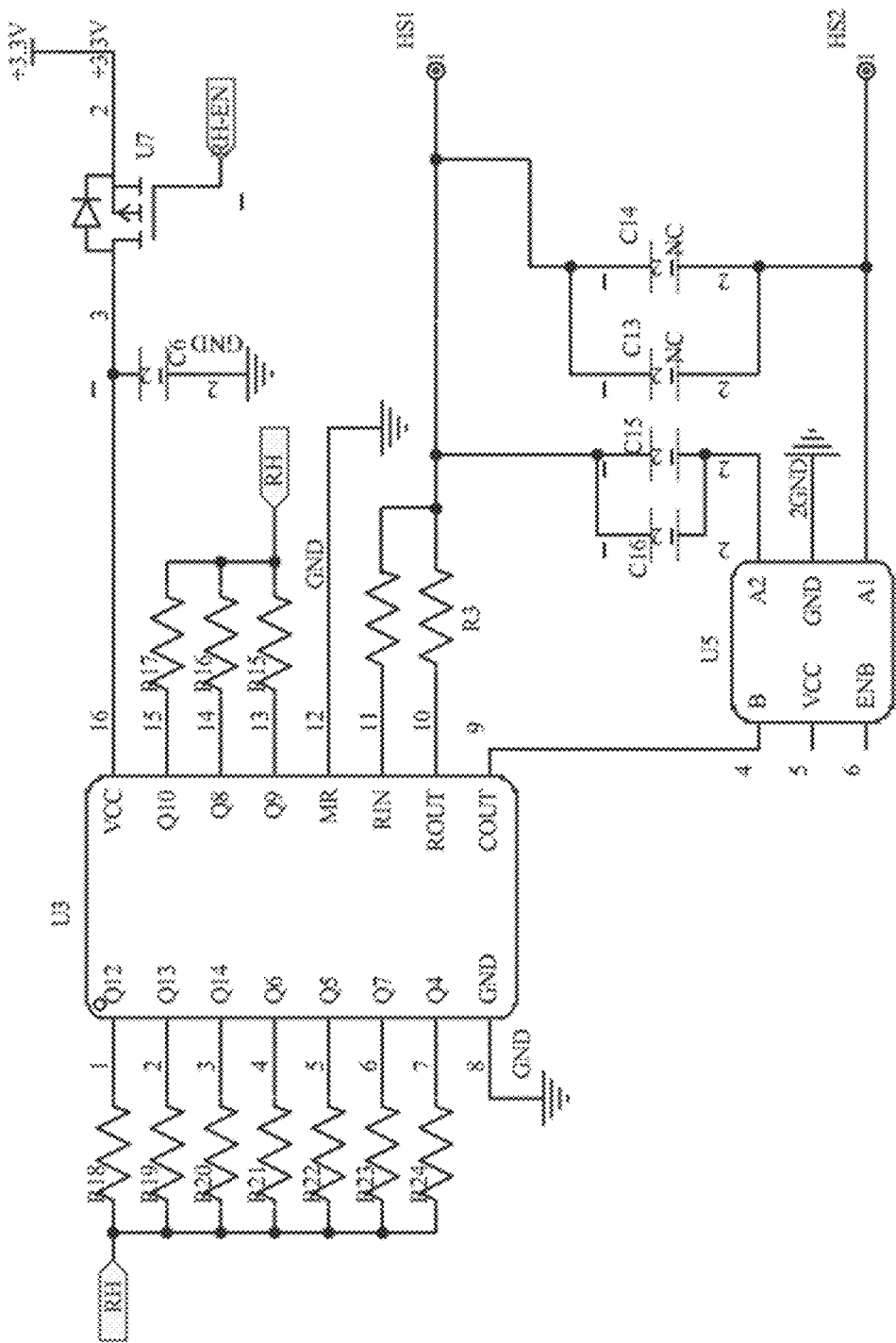
FIG. 6 is a circuit structure diagram of the moisture measurement circuit with the frequency square wave chip and a selection chip according to a specific implementation mode.

In some embodiments, the moisture measurement circuit further includes a frequency square wave chip (FIG. 5, U3) and a third resistor (FIG. 5, R3), a first capacitor pin (FIG. 5, U3 COUT) of the frequency square wave chip is connected to one of the electrode pieces 30, an adjacent other electrode piece 30 is connected to an end of the third resistor, and the other end of the third resistor is connected to a second capacitor pin (FIG. 5, U3 ROUT) of the frequency square wave chip; a frequency output pin (FIG. 5, U3-RH) of the frequency square wave chip is connected to a frequency receiving pin (FIG. 5, U1-PA0) of the main control chip. In this embodiment, the frequency square wave chip sends a corresponding frequency square wave signal to the main control chip after receiving the capacitance change between the electrode pieces 30, and the main control chip calculates and obtains the corresponding humidity data after receiving the frequency signal. In an implementation mode, the moisture measurement circuit further includes a selection chip (FIG. 6, U5), a first regulating capacitor group (FIG. 6, C13, C14), and a second regulating capacitor group (FIG. 6, C15, C16). The first regulating capacitor group and the second regulating capacitor group are both composed of multiple capacitors that are arranged in parallel, and an access pin of the selection chip (FIG. 6, U5-B) is connected to the first capacitor pin (FIG. 6, U3-COUT) of the frequency square wave chip, an end of the first regulating capacitor group is connected to a first output pin (FIG. 6, U5-A1) of the selection chip and one of the electrode pieces 30. The other end of the first regulating capacitor group is connected to the second capacitor pin (FIG. 6, U3-ROUT) of the frequency square wave chip and the other adjacent electrode piece 30. An end of the second regulating capacitor group is connected to the first output pin (FIG. 6, U5-A2) of the selection chip and one of the electrode pieces 30, the other end of the second regulating capacitor group is connected to a second capacitor pin of the frequency square wave chip (FIG. 6, U3 ROUT) and the other adjacent electrode piece 30. The capacitance of the first regulating capacitor group and the capacitance of the second regulating capacitor group can be set differently according to different actual usage scenarios. The specific capacitance value should be determined based on the measured soil moisture value and range. By selecting the chip, different connection circuits can be switched, and capacitance will be changed, fast switching is achieved, it can be compatibility with multiple different usage scenarios, and thereby improving its practicality. In an implementation mode the frequency square wave chip includes multiple different division pins (FIG. 6, Q4-Q14), and the detection pin of the main control chip is connected to one of the division pins. Specifically, the multiple division pins of the frequency square wave chip can correspond to different division frequencies, and different division frequencies can be achieved by switching division frequencies to transmit square wave signals with different frequencies. The main control chip receives square wave signals with different frequencies, and a more accurate moisture detection is achieved.

The present disclosure further provides a soil detection system, which is an upper-level integrated system, and includes a data acquisition module, a display module, an information transmission module, and an information storage module. Multiple soil moisture detection devices described in the above embodiments can be provided in different locations of the soil, humidity data is collected and transmitted back to the system for calculation and integration. In addition, the system can add corresponding sensors according to detection requirements, such as parameters of soil conductivity, groundwater level, groundwater quality, air humidity, air temperature, and light intensity.

It should be noted that although the above embodiments have been described in this specification, it does not limit the protection scope of the present disclosure. Therefore, based on the innovative concept of the present disclosure, any changes and modifications made to the embodiments described herein, or equivalent structural or process transformations made using the description and drawings of the present disclosure, directly or indirectly applying the above technical solutions to other related technical fields, are all within the protection scope of the present disclosure.

What is claimed is:

1. A capacitive soil moisture detection device, comprising a substrate, an outer shell, a circuit board, and a main control chip, wherein the main control chip is provided on the circuit board, the circuit board is provided with a moisture measurement circuit that is arranged in the outer shell; a connection end of the substrate is clamp connection to the outer shell;

wherein an inner of the substrate is provided with at least two electrode pieces, the electrode pieces are facing to each other and arranged spaced apart; each electrode piece is coated with a substrate material; a pin of one of the electrode pieces is connected to the main control chip, and an adjacent other electrode piece is provided with a grounding terminal.

2. The capacitive soil moisture detection device according to claim 1, wherein the substrate is a PCB board.

3. The capacitive soil moisture detection device according to claim 2, wherein the substrate comprises a front plate, a middle plate, and a rear plate.

4. The capacitive soil moisture detection device according to claim 1, wherein the substrate is provided with a series of holes, which are arranged along an edge of the substrate.

5. The capacitive soil moisture detection device according to claim 1, wherein an outer surface of the substrate is covered with a reinforcing layer.

6. The capacitive soil moisture detection device according to claim 1, wherein the moisture measurement circuit further comprises a first resistor, wherein one pin of one of the electrode pieces is respectively connected to a detection pin of the main control chip and an end of the first resistor; the other end of the first resistor is connected to a signal output pin of the main control chip.

7. The capacitive soil moisture detection device according to claim 6, wherein the moisture measurement circuit further comprises a first capacitor, one pin of one of the electrode pieces is respectively connected to a detection pin of the main control chip and an end of the first resistor through the first capacitor.

8. The capacitive soil moisture detection device according to claim 6, wherein the moisture measurement circuit further comprises a second capacitor, two ends of the second capacitor are respectively connected to a pin of one of the electrode pieces and the grounding terminal of another one of the electrode pieces.

9. The capacitive soil moisture detection device according to claim 6, wherein the moisture measurement circuit further comprises a second resistor, an end of the second resistor is connected to an end of the first resistor, and the other end of the second resistor is connected to another signal output pin of the main control chip.

10. The capacitive soil moisture detection device according to claim 1, wherein the moisture measurement circuit further comprises a frequency square wave chip and a third resistor, wherein a first capacitor pin of the frequency square wave chip is connected to one of the electrode pieces, an adjacent other electrode piece is connected to an end of the third resistor, and the other end of the third resistor is connected to a second capacitor pin of the frequency square wave chip; a frequency output pin of the frequency square wave chip is connected to a frequency reception pin of the main control chip.

11. The capacitive soil moisture detection device according to claim 10, wherein the moisture measurement circuit further comprises a selection chip, a first regulating capacitor group, and a second regulating capacitor group; an access pin of the selection chip is connected to the first capacitor pin of the frequency square wave chip;

an end of the first regulating capacitor group is connected to a first output pin of the selection chip and one of the electrode pieces, and the other end of the first regulating capacitor group is connected to a second capacitor pin of the frequency square wave chip and the other adjacent electrode piece;

an end of the second regulating capacitor group is connected to the first output pin of the selection chip and one of the electrode pieces, the other end of the second regulating capacitor group is connected to the second capacitor pin of the frequency square wave chip and the other adjacent electrode piece.

12. The capacitive soil moisture detection device according to claim 10, wherein the frequency square wave chip comprises multiple different division pins, and the detection pin of the main control chip is connected to one of the division pins.

13. A detection system, comprising the capacitive soil moisture detection device according to claim 1.

14. A detection system, comprising the capacitive soil moisture detection device according to claim 2.

15. A detection system, comprising the capacitive soil moisture detection device according to claim 3.

16. A detection system, comprising the capacitive soil moisture detection device according to claim 4.

17. A detection system, comprising the capacitive soil moisture detection device according to claim 5.

18. A detection system, comprising the capacitive soil moisture detection device according to claim 6.

19. A detection system, comprising the capacitive soil moisture detection device according to claim 7.

20. A detection system, comprising the capacitive soil moisture detection device according to claim 8.

* * * * *